United States Patent
Akbar

(10) Patent No.: US 12,279,908 B2
(45) Date of Patent: Apr. 22, 2025

(54) LABOR GARMENT FACILITATING ADMINISTRATION OF AN EPIDURAL AND MAINTAINING MONITORING TRANSDUCERS IN PLACE

(71) Applicant: A. NIsar Akbar, Mequon, WI (US)

(72) Inventor: A. NIsar Akbar, Mequon, WI (US)

( * ) Notice: Subject to any disclaimer, the term of this patent is extended or adjusted under 35 U.S.C. 154(b) by 243 days.

(21) Appl. No.: 17/456,640

(22) Filed: Nov. 28, 2021

(65) Prior Publication Data

US 2022/0211343 A1  Jul. 7, 2022

Related U.S. Application Data

(60) Provisional application No. 63/199,524, filed on Jan. 5, 2021.

(51) Int. Cl.
*A61B 8/00* (2006.01)
*A41B 9/14* (2006.01)

(52) U.S. Cl.
CPC .............. *A61B 8/4227* (2013.01); *A41B 9/14* (2013.01)

(58) Field of Classification Search
CPC ....... A61B 8/4227; A61B 8/0866; A41B 9/14; A41C 1/10
See application file for complete search history.

(56) References Cited

U.S. PATENT DOCUMENTS

| | | | | | |
|---|---|---|---|---|---|
| 1,828,015 | A | * | 10/1931 | Allebach | A41C 1/10 450/155 |
| 1,920,648 | A | * | 8/1933 | Lane | A61F 5/40 602/70 |
| 2,606,322 | A | * | 8/1952 | Vraciu | A41C 1/10 2/221 |
| 3,273,563 | A | * | 9/1966 | Bonang | A61F 5/03 450/96 |
| 4,108,149 | A | * | 8/1978 | Castiglia | A41C 1/10 450/155 |
| 4,836,824 | A | * | 6/1989 | Seering | A41C 1/10 450/155 |
| 5,060,639 | A | * | 10/1991 | Marcus | A61F 5/028 128/95.1 |
| 5,094,648 | A | * | 3/1992 | Turner | A41C 1/10 2/73 |
| 5,571,039 | A | * | 11/1996 | Ford | A41C 1/10 2/45 |
| 5,702,286 | A | * | 12/1997 | Seering | A41C 1/10 2/45 |

(Continued)

FOREIGN PATENT DOCUMENTS

| | | |
|---|---|---|
| WO | 96/08217 A1 | 3/1996 |
| WO | 2005/110236 A1 | 11/2005 |
| WO | WO-2021019221 A1 * | 2/2021 |

OTHER PUBLICATIONS

Internet Ad, Nu-Hope Laboratories, (https://parthenoninc.com/brands/Nu%252dHop Laboratories.html), accessed Jul. 16, 2020.

*Primary Examiner* — Khaled Annis
(74) *Attorney, Agent, or Firm* — Lawrence S Pope

(57) ABSTRACT

The disclosure concerns a stretchable garment adapted to be worn by a woman in labor to hold one or more monitoring transducers in place during the course of labor and delivery. It comprises a fabric body that encircles the torso of the woman including her belly and has an aperture which allows access to between L2 and S1 of her lumbar spine.

5 Claims, 4 Drawing Sheets

(56) References Cited

U.S. PATENT DOCUMENTS

| | | | |
|---|---|---|---|
| 5,746,776 A | 6/1998 | Francis | |
| 5,865,820 A * | 2/1999 | Myello | A61F 5/445 |
| | | | 2/312 |
| 5,946,944 A * | 9/1999 | Osborne | D04B 1/102 |
| | | | 450/92 |
| 6,817,034 B2 * | 11/2004 | Smilovic | A41D 1/21 |
| | | | 2/73 |
| 7,716,753 B2 * | 5/2010 | Franko | A41B 9/002 |
| | | | 2/400 |
| 8,087,098 B2 * | 1/2012 | Kimberly | A41B 9/001 |
| | | | 2/403 |
| 8,911,371 B2 | 12/2014 | George et al. | |
| 9,282,774 B2 * | 3/2016 | Martin | A41B 9/001 |
| 9,456,637 B2 * | 10/2016 | Fligel | A41C 1/10 |
| 9,730,476 B1 * | 8/2017 | Mahar | A41D 1/21 |
| 9,737,095 B1 * | 8/2017 | Kitelinger | H04R 1/028 |
| 10,010,193 B2 * | 7/2018 | Simmer | A41D 1/18 |
| 10,045,569 B2 * | 8/2018 | Caden | A41C 1/08 |
| 10,463,527 B2 * | 11/2019 | Gallant | A61F 5/4408 |
| 10,470,501 B2 * | 11/2019 | Caden | A41D 1/21 |
| 11,357,266 B1 * | 6/2022 | Connors | A41B 9/005 |
| 2003/0171068 A1 * | 9/2003 | Cosentino | A61F 5/03 |
| | | | 450/155 |
| 2005/0256466 A1 * | 11/2005 | Winkler | A61F 5/449 |
| | | | 604/332 |
| 2007/0174950 A1 * | 8/2007 | Gidish | A41C 1/003 |
| | | | 2/406 |
| 2009/0055998 A1 * | 3/2009 | Blumenfeld | A41B 9/14 |
| | | | 2/403 |
| 2009/0108205 A1 * | 4/2009 | Duffy | A61B 5/14553 |
| | | | 250/339.07 |
| 2010/0262056 A1 * | 10/2010 | Lusky | A61F 5/028 |
| | | | 602/19 |
| 2011/0016614 A1 * | 1/2011 | Okada | A41B 9/004 |
| | | | 2/240 |
| 2011/0076921 A1 * | 3/2011 | Unger | A41C 1/08 |
| | | | 450/156 |
| 2011/0118640 A1 | 5/2011 | Pollack | |
| 2012/0122372 A1 * | 5/2012 | Fong | A41C 1/10 |
| | | | 450/155 |
| 2012/0311758 A1 * | 12/2012 | Nicholson | A41D 27/20 |
| | | | 2/400 |
| 2014/0058307 A1 | 2/2014 | Marshall | |
| 2014/0196196 A1 * | 7/2014 | Lee | A41F 7/00 |
| | | | 2/400 |
| 2014/0221892 A1 * | 8/2014 | Javaid | A61F 5/028 |
| | | | 602/19 |
| 2014/0259305 A1 * | 9/2014 | Martin | A41B 9/001 |
| | | | 2/400 |
| 2015/0320121 A1 * | 11/2015 | Fligel | A41C 1/10 |
| | | | 450/155 |
| 2016/0183873 A1 * | 6/2016 | Lin | A61B 5/344 |
| | | | 600/301 |
| 2016/0228278 A1 * | 8/2016 | Wang | A61F 5/028 |
| 2018/0007977 A1 * | 1/2018 | Windenberger | A41C 1/10 |
| 2018/0146868 A1 * | 5/2018 | Pon | A61B 8/0866 |
| 2019/0125593 A1 * | 5/2019 | Xiong | A61F 13/491 |
| 2019/0274374 A1 * | 9/2019 | Marconi | A41B 9/026 |
| 2020/0093192 A1 * | 3/2020 | Strottner | A41C 1/10 |
| 2020/0205493 A1 * | 7/2020 | May Woodruff | A41D 13/1281 |
| 2021/0205113 A1 * | 7/2021 | Wong | A61F 5/028 |
| 2021/0308477 A1 * | 10/2021 | Myakishev-Rempel | A61N 2/002 |
| 2022/0000675 A1 * | 1/2022 | Bourdillon | A61F 13/145 |
| 2022/0211343 A1 * | 7/2022 | Akbar | A41B 9/14 |

* cited by examiner

LABOR GARMENT FACILITATING ADMINISTRATION OF AN EPIDURAL AND MAINTAINING MONITORING TRANSDUCERS IN PLACE

BACKGROUND OF THE INVENTION

Medical staff routinely monitor the progress of pregnant woman during labor and delivery with one or more transducers that report on the uterine contractions and the fetal heartbeat or fetal heart tones. To function properly these transducers need to be held in position during the progress of the labor to delivery, particularly when the patient is sitting up for epidural placement. They require a particular type of interface with the skin of the woman in labor, typically a gel that has been applied to a specific location. In addition, these transducers are typically calibrated based on their relative positions to the uterus of the woman. Adhesives and belts have been employed but are not entirely satisfactory. The adhesives are adversely affected by sweat developing on the skin of the woman and the belts have a tendency to slip, especially given the concern that they not be so tightly cinched as to cause undue discomfort to the woman in labor. Therefore, the practice has developed to use a garment, which looks like a band, that encompasses the torso of the woman covering her belly and the adjacent portion of her back to hold these transducers in place. This garment or band has been used to cover adhesives and belts. However, the mechanical configuration of such garments prevents easy access to the lower spine of the woman including the lumbar spine region between L2 and S1 that is important for the administration of epidural injection and placement of continuous labor epidural with a catheter. Thus, the garments or bands currently being used are not designed to accommodate for placement of an epidural. The current garment must be moved either up or way down to expose the lumbar spine for epidural administration. This movement of the garment adversely effects the reliability of the signal from the relevant transducer making it very difficult to monitor the fetal heart tones. From the time the patient is sitting up for an epidural to lying down is on average about 15 minutes. If the fetal heart tones cannot be monitored for that long, it puts the welfare of unborn baby in jeopardy. In addition, these garments or bands are not designed to provide dignified comfort and care to pregnant women.

SUMMARY OF THE INVENTION

The present invention involves a stretchable garment adapted to be worn by a woman in labor to hold one or more monitoring transducers in place during labor and delivery. It comprises a crotchless fabric body that encircles the torso of the woman including her belly above her crotch area having an aperture on a back side centered over the lumbar spine to allow access to between L2 and S1 of her lumbar spine. Conveniently the garment may have a unitary one piece and strapless configuration and the fabric body may be bounded by an upper edge and a lower edge with said edges and the material between them entirely encircling said torso and bounding said aperture. The garment is designed to provide comfort and dignity to the new mom to be, as the parents welcome their new baby to the family.

DETAILED DESCRIPTION

Figure 1:
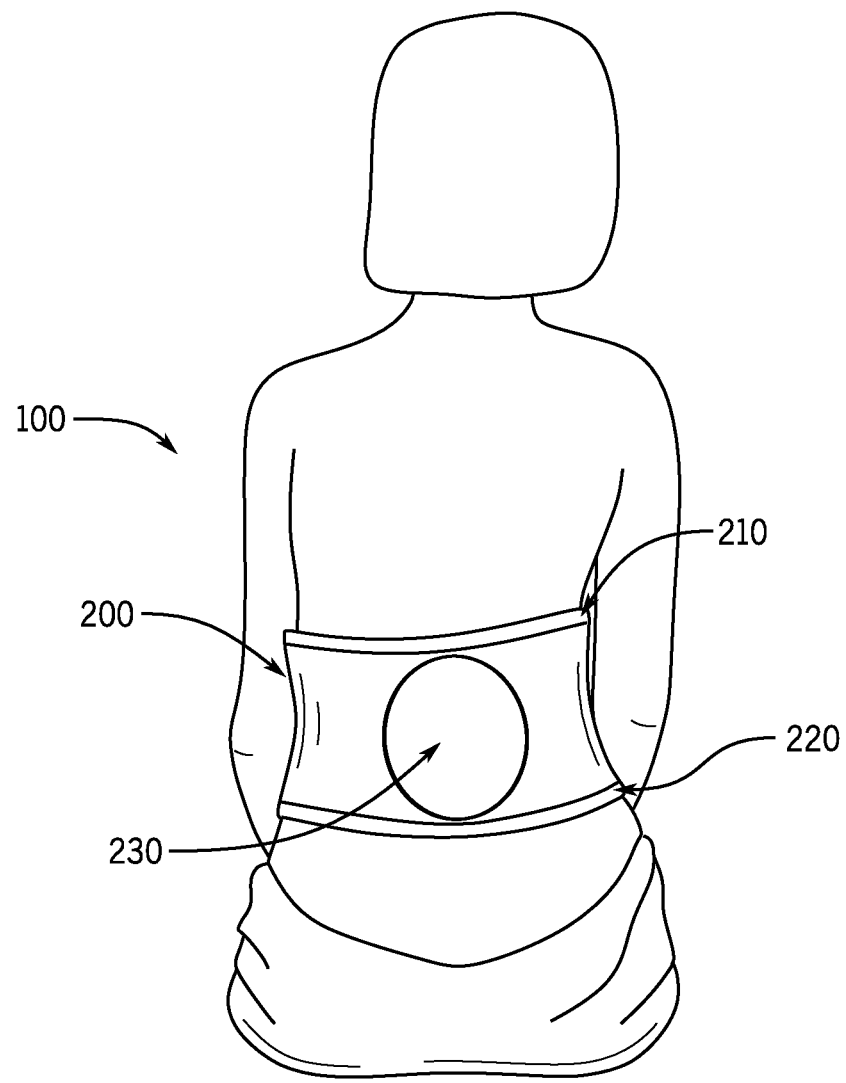
FIG. 1 is a perspective view of the back of a woman in labor seated wearing a labor garment.

FIG. 1 illustrates a crotchless labor garment 200 on the torso of a woman in labor 100 in a sitting position. Garment 200 has a top band 210 and a bottom band 220 which aid in affixing the garment 200 to the torso of the woman and retain it in its desired position. This garment 200 also has an aperture 230 which aligns with the lumbar spine of the woman 100 and provides easy access to the portion of her lumbar spine between L2 and S1. This facilitates the administration of an epidural by an anesthesiologist without disturbing the positioning of the garment 200. The garment 200 may be quite similar to that disclosed in U.S. Pat. No. 9,456,637 to Fligel of Garan, incorporated by reference herein, with a modification to provide an aperture 230. It is desirable that the garment 200 be so designed that movement between it and the torso of the woman is minimized through the course of labor and delivery.

Figure 2:
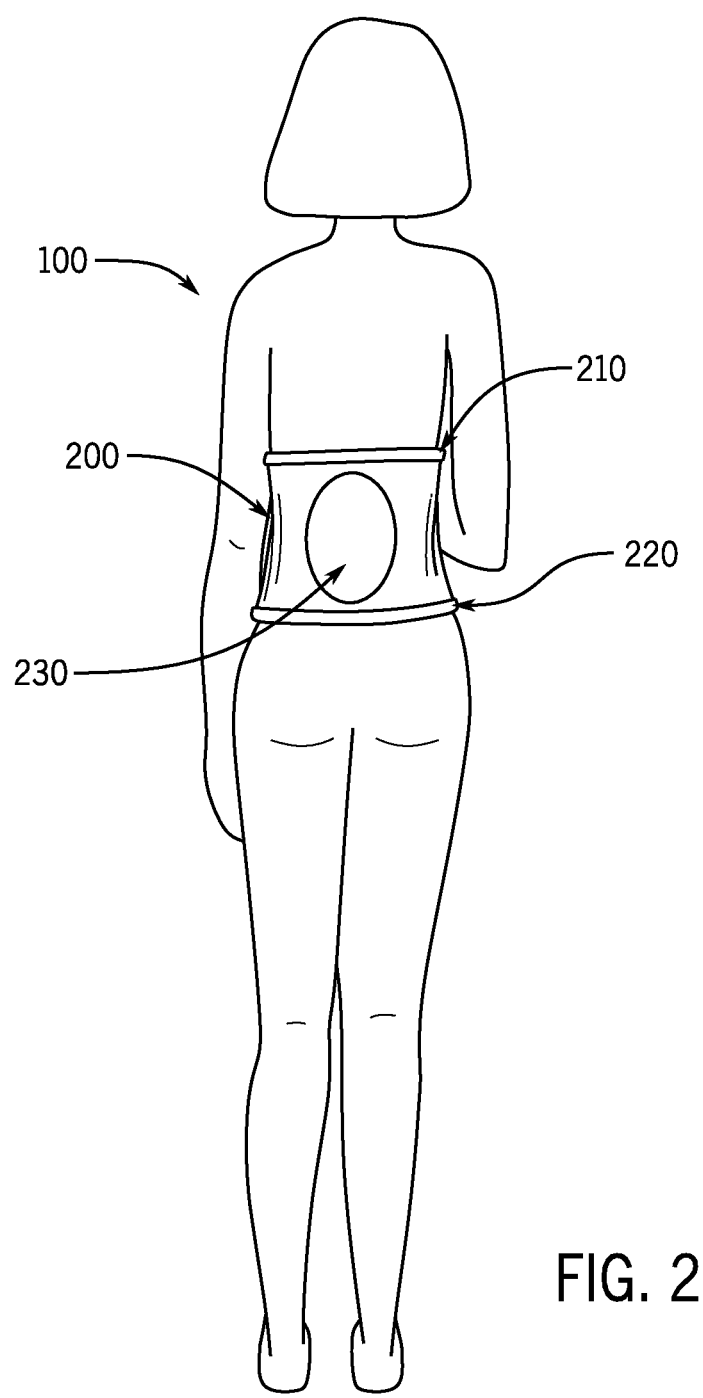
FIG. 2 is a perspective view of the back of a woman in labor standing wearing a labor garment.

FIG. 2 illustrates that the garment 200 stays in position on the torso of the woman 100 when she is in a standing position with the aperture 230 aligned with the lumbar spine. In this regard it is desirable that placing the woman 100 in various positions during her labor and delivery process will not affect the position of the garment 200 on her torso.

Figure 3:
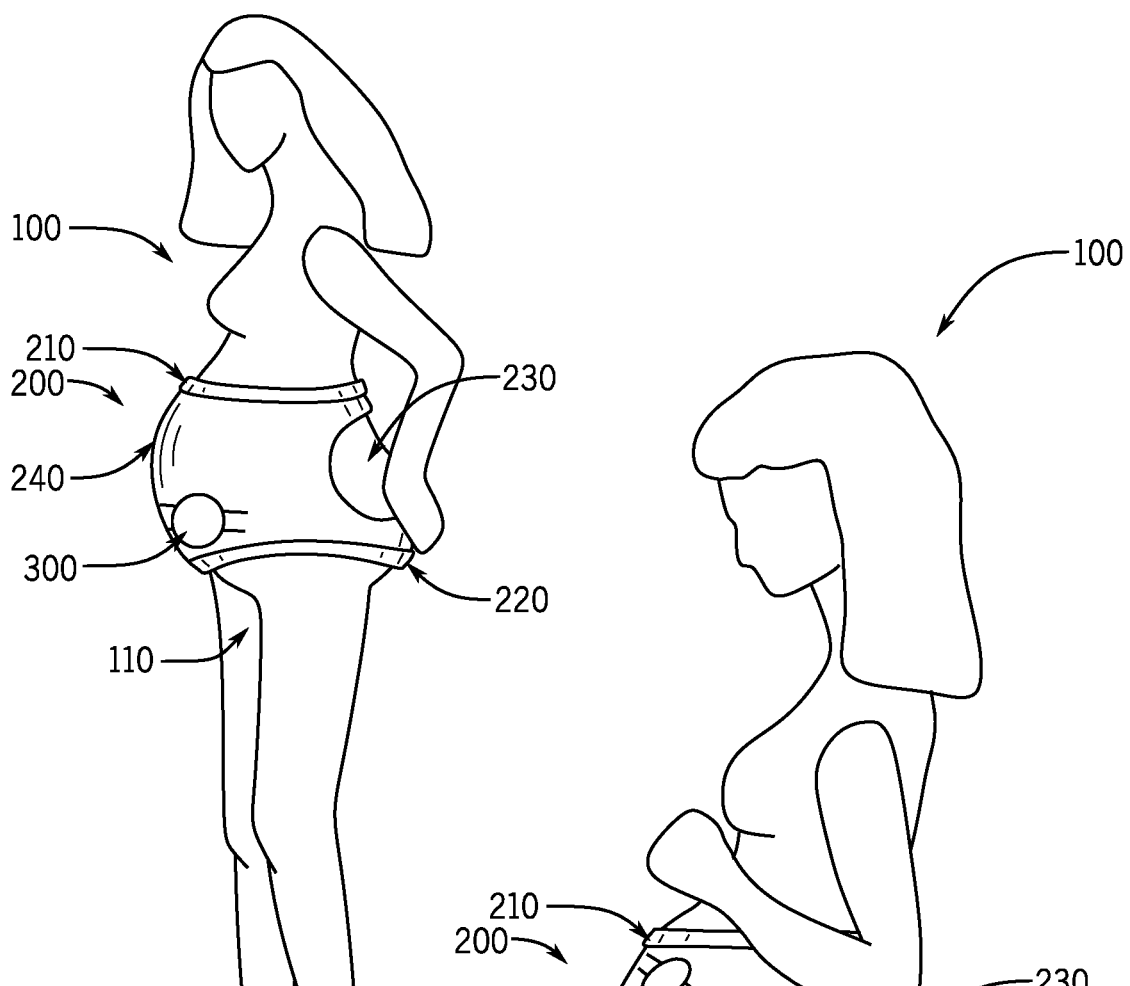
FIG. 3 is a profile perspective view of a woman in labor standing wearing a labor garment.

FIG. 3 illustrates the garment 200 with a pouch 240 that accommodates, receives and supports the belly of the woman 100. This configuration may be aided by having the distance between the top band 210 and the bottom band 220 be greater in the portion of the garment 200 that covers the belly of the woman 100 than in the portion that covers the remainder of the torso including the back of the woman 100 in the manner disclosed in U.S. Pat. No. 9,456,637. The garment 200 covers a transducer 300 that monitors either the labor contractions or the fetal hear beat or both in the manner of U.S. Pat. No. 4,966,152 to Gang et al. of Hewlett-Packard, incorporated by reference herein. This transducer 300 may simply lie beneath the garment 200 or it may be held in a pocket of the garment 200. In the latter case the pocket needs to be configured to allow the transducer 300 to contact the skin of the woman 100. The transducer 300 may be affixed to the skin of the woman 100 by an appropriate adhesive or it may simply contact this skin via an appropriate ultrasound transmitting gel. In either case the garment makes a significant contribution to retaining the transducer 300 in an appropriate location. Commonly the transducer 300 is position to receive an optimum signal representative of the fetal heart beat and is calibrated in accordance with its position. In this regard a particularly desirable location for the placement of a toco probe for simultaneous monitoring of the labor contractions and the fetal heart beat is adjacent to the umbilicus on the fondus of the uterus. Thus, obviating any need to move the garment 200 to administer an epidural to the lumbar spine by providing the aperture 230 facilitates obtaining an uninterrupted and reliable signal of the fetal heart beat while an epidural is administered.

Figure 4:
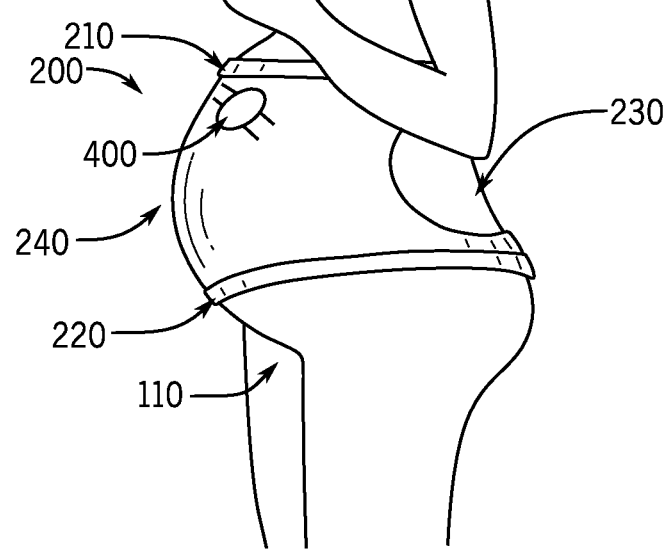
FIG. 4 is a profile perspective view of a woman in labor standing wearing a labor garment.

FIG. 4 illustrates the same features as FIG. 3 with the exception that it has a transducer 400 in a different location than the transducer 300 illustrated in FIG. 3. There are a variety of reasons why it might be advantageous to use more than one transducer to monitor labor contractions and the fetal heartbeat. Among others is the fact that as explained in U.S. Pat. No. 4,966,152 the optimum locations for a toco transducer to monitor the labor contractions may differ from the transducer for monitoring the fetal heartbeat.

Figure 5:
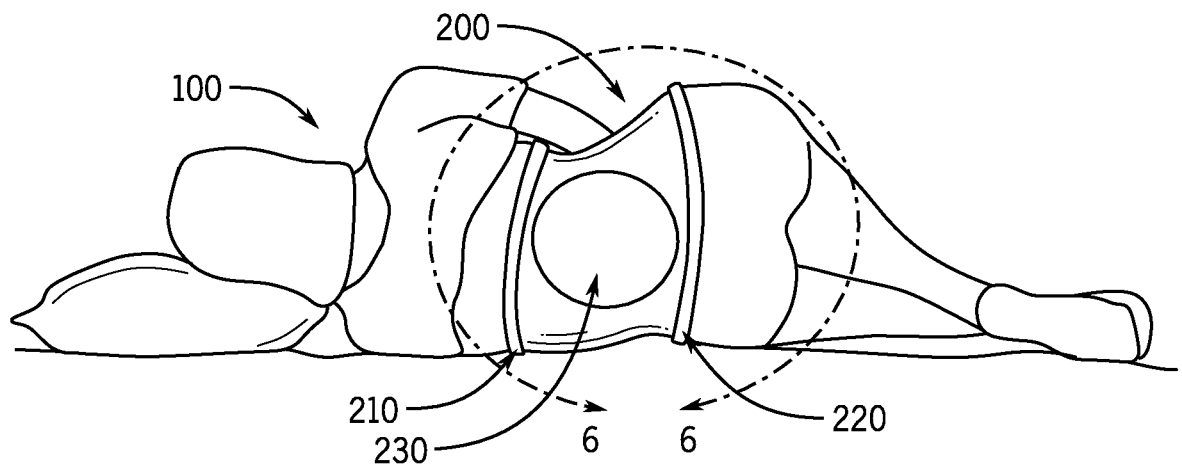
FIG. 5 is a perspective view of the back of a woman in labor lying on her side wearing a labor garment.

FIG. 5 illustrates the woman 100 lying on her side. with her back facing the viewer. It displays the same features as FIG. 2. The aperture 230 provides easy access to the lumbar spine between L2 and S1 so that an epidural could be administered without any need to move the garment 200 and any transducer that it may be holding in place.

Figure 6:
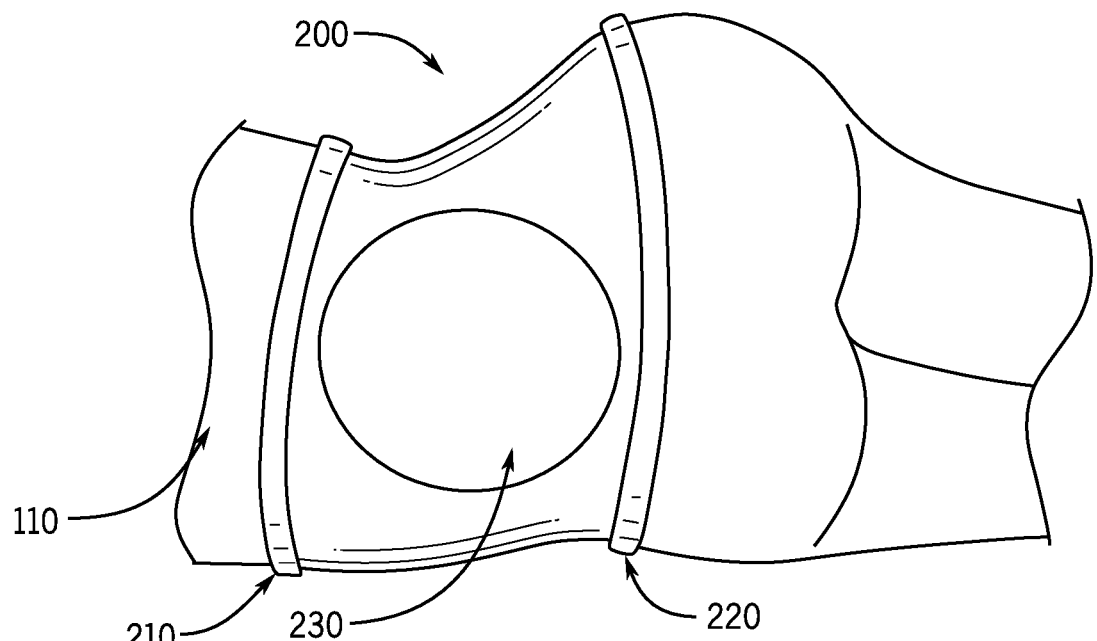
FIG. 6 is an expanded view indicated by line 6-6 of the woman and labor garment illustrated in FIG. 5.

FIG. 6 is an expanded view defined by lines 6-6 of FIG. 5 of the lumbar spine region 110 of the woman 100 with the garment 200 and its aperture 230 properly placed to facilitate the administration of an epidural.

The garment 200 may have any number of designs and may be made of a wide variety of materials. It is conveniently stretchable so it can be readily slipped over the torso of a woman 100 either starting from either the head or the feet. It is advantageous if it applies enough elastic force to the torso of the woman 100 that it is able to hold one or more transducers in place and maintain its aperture 230 over the appropriate portion of the lumbar spine throughout the course of labor and delivery without causing undue discomfort to the woman 100. A design which has a pouch for encompassing the belly of the woman in labor 100 such as that disclosed in U.S. Pat. No. 9,456,637 is convenient as is constructing the garment 200 with soft fibers, at least some of which are elastic.

The garment 200 may be applied to the woman in labor 100 after she arrives at the birthing hospital and advantageously after any desired monitoring transducers 300 and 400 and associated ultrasound transmission gels have been applied to their desired locations. If the garment is to be applied to a woman 100 in active labor, it may be convenient to provide a break in the garment 200 so that it can be wrapped about the woman 100 instead of being slipped over her torso. In such a case the garment 200 would be provided with fastening means such as snaps, clips, a zipper or Velcro strips to close the break.

The garment 200 could be supplied to the woman 100 in advance of her presenting at the birthing hospital. This would allow her to don it when her labor was less active so that the slipping on of the garment 200 would involve less discomfort.

It is desirable that the garment 200 stays in position on the torso of the woman 100 regardless of whether she is in a standing, sitting or lateral position with the aperture 230 aligned with the lumbar spine.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A garment adapted to be worn by a woman in labor to hold one or more monitoring transducers in place during the course of labor and delivery comprising a stretchable, crotchless, unitary one piece fabric body free of straps bounded by an upper edge and a lower edge with said edges and the material between them entirely encircling the torso of the woman including her belly above her crotch area, said edges and the material between them bounding an aperture on a back side which is adapted to be centered over the lumbar spine to allow access to the area between L2 and S1 of her lumbar spine;
   wherein the garment has a pouch that is adapted to substantially encompass and substantially cover the entire surface of the belly such that it receives and supports the belly and is located on the opposite side of the garment from the aperture.

2. The garment of claim 1 wherein there is minimal movement between the garment and the torso throughout the course of a normal labor and delivery.

3. The garment of claim 1 wherein it is constructed of soft fibers with elastic elements.

4. The garment of claim 1 adapted to stay in in position regardless of the position of the woman.

5. The garment of claim 4 wherein there is minimal movement between the garment and the torso of the woman when she is placed in a sitting position.

* * * * *